United States Patent
Büttner et al.

(10) Patent No.: US 11,455,531 B2
(45) Date of Patent: Sep. 27, 2022

(54) TRUSTWORTHY PREDICTIONS USING DEEP NEURAL NETWORKS BASED ON ADVERSARIAL CALIBRATION

(71) Applicant: Siemens Aktiengesellschaft, Munich (DE)

(72) Inventors: Florian Büttner, Munich (DE); Christian Tomani, Munich (DE)

(73) Assignee: SIEMENS AKTIENGESELLSCHAFT

(*) Notice: Subject to any disclaimer, the term of this patent is extended or adjusted under 35 U.S.C. 154(b) by 527 days.

(21) Appl. No.: 16/653,415

(22) Filed: Oct. 15, 2019

(65) Prior Publication Data
US 2021/0110253 A1 Apr. 15, 2021

(51) Int. Cl.
*G06N 3/08* (2006.01)
*G06K 9/62* (2022.01)
*G06F 17/18* (2006.01)

(52) U.S. Cl.
CPC ............... *G06N 3/08* (2013.01); *G06F 17/18* (2013.01); *G06K 9/6256* (2013.01)

(58) Field of Classification Search
CPC ........ G06N 3/08; G06N 3/084; G06N 3/0454; G06N 3/0472; G06N 20/00; G06N 3/04; G06N 3/088; G06N 3/0445; G06N 5/04; G06N 3/0481; G06F 17/18; G06K 9/6256; G06K 9/6262; G06K 9/6257; G06K 9/6215; G06K 9/6267; G06K 9/6271; G06V 10/82; G06V 20/40; G06V 20/41; G06V 40/16; G06V 40/168; A61B 5/0035; A61B 5/7267; G06T 2207/20081; G06T 2207/20084; G06T 3/4046; G06T 7/11; G06T 2207/30096; G06T 3/4053; G06T 5/001; G06T 5/002; G06T 5/50; G06T 7/0012

See application file for complete search history.

(56) References Cited

U.S. PATENT DOCUMENTS

| | | | |
|---|---|---|---|
| 11,055,822 B2* | 7/2021 | Ramanujam | G06F 16/53 |
| 11,126,891 B2* | 9/2021 | St. Romain, II | G06T 19/00 |
| 2019/0130583 A1* | 5/2019 | Chen | G06T 7/11 |
| 2019/0147220 A1* | 5/2019 | McCormac | G06V 20/64 382/103 |
| 2019/0188510 A1* | 6/2019 | Han | G06V 40/172 |
| 2019/0295223 A1* | 9/2019 | Shen | G06V 20/10 |
| 2019/0369598 A1* | 12/2019 | Kubo | G05B 19/4065 |
| 2020/0005168 A1* | 1/2020 | Bhargava | G06N 5/022 |
| 2020/0265307 A1* | 8/2020 | Suh | G06N 3/08 |
| 2020/0293783 A1* | 9/2020 | Ramaswamy | G06V 20/40 |
| 2021/0067807 A1* | 3/2021 | Lainema | H04N 19/184 |
| 2021/0105451 A1* | 4/2021 | Oyman | H04L 65/65 |

(Continued)

*Primary Examiner* — Michael S Osinski
(74) *Attorney, Agent, or Firm* — Schmeiser, Olsen & Watts LLP

(57) ABSTRACT

The disclosed relates to a computer-implemented method of training a Neural Network as well as a corresponding computer program, computer-readable medium and data processing system. In addition to a categorical cross-entropy loss $L_{CCE}$ weights of the NN are updated based on predictive entropy loss $L_S$ and an adversarial calibration loss $L_{adv}$.

10 Claims, 4 Drawing Sheets

(56) References Cited

U.S. PATENT DOCUMENTS

| | | | |
|---|---|---|---|
| 2021/0158161 A1* | 5/2021 | Louizos | G06N 3/08 |
| 2021/0248716 A1* | 8/2021 | Vera-Gonzalez | G06T 7/174 |
| 2021/0272253 A1* | 9/2021 | Lin | G06V 40/161 |
| 2021/0279513 A1* | 9/2021 | Jie | G06V 10/255 |
| 2021/0326576 A1* | 10/2021 | Liang | G06V 40/168 |
| 2021/0374907 A1* | 12/2021 | Su | G06T 3/4053 |
| 2021/0374913 A1* | 12/2021 | Su | G06T 5/002 |
| 2021/0407041 A1* | 12/2021 | Liu | G06N 3/084 |
| 2021/0407086 A1* | 12/2021 | Liu | G06T 7/0012 |
| 2022/0004848 A1* | 1/2022 | Hoydis | G06N 3/088 |
| 2022/0012898 A1* | 1/2022 | Carreira | G06T 5/50 |
| 2022/0019855 A1* | 1/2022 | Chen | G06K 9/6257 |
| 2022/0027536 A1* | 1/2022 | Dutta | G06N 20/00 |
| 2022/0051416 A1* | 2/2022 | Cao | G06T 7/215 |
| 2022/0067115 A1* | 3/2022 | Zheng | G06N 5/02 |
| 2022/0067442 A1* | 3/2022 | Masse | G06V 10/82 |
| 2022/0121902 A1* | 4/2022 | Hann | G06N 3/0454 |
| 2022/0148299 A1* | 5/2022 | Bonnevie | G06N 3/0472 |

\* cited by examiner

TRUSTWORTHY PREDICTIONS USING DEEP NEURAL NETWORKS BASED ON ADVERSARIAL CALIBRATION

FIELD OF TECHNOLOGY

The present invention relates to a computer-implemented method of training a Neural Network (NN) as well as a corresponding computer program, computer-readable medium and data processing system.

BACKGROUND

To facilitate a wide-spread acceptance of AI systems guiding decision making in real-world applications, trustworthiness of deployed models is key. Not only in safety-critical applications such as autonomous driving or Computer-aided Diagnosis Systems (CDS), but also in dynamic open world systems in industry it is crucial for predictive models to be uncertainty-aware and yield well-calibrated (and thus trustworthy) predictions for both in-domain samples ("known unknowns") as well as out-of-domain samples ("unknown unknowns"). In particular, in industrial and IoT settings deployed models may encounter erroneous and inconsistent inputs far away from the input domain throughout the life-cycle. In addition, the distribution of the input data may gradually move away from the distribution of the training data (e.g. due to wear and tear of the assets, maintenance procedures or change in usage patterns etc.). The importance of technical robustness and safety in such settings is also highlighted by the recently published "Ethics guidelines for trustworthy AI" by the European Commission (https://ec.europa.eu/digital-single-market/en/news/ethics-guidelines-trustworthy-ai), requiring for trustworthy AI to be lawful, ethical and robust (technically and taking into account its social environment).

Common approaches to account for predictive uncertainty include post-processing steps for trained NNs, where for example a validation set, drawn from the same distribution as training data, is used to rescale the logit vectors returned by a trained NN such that in-domain predictions are well calibrated. Orthogonal approaches have been proposed where trust scores and other measures for out-of-distribution detection are derived, typically also based on trained networks. Alternative avenues towards intrinsically uncertainty-aware networks have been followed by training probabilistic models. In particular, a lot of research effort has been put into training Bayesian NNs, where typically a prior distribution over the weights is specified and, given the training data, a posterior distribution over the weights is inferred. This distribution can then be used to quantify predictive uncertainty. Since exact inference is untraceable, a range of approaches for approximate inference has been proposed, including deterministic approaches such as variational inference, Laplace approximation, expectation propagation, as well as Markov Chain Monte Carlo (MCMC) methods with Hamiltionian dynamics and Langevin diffusion methods. In particular deterministic approaches based on variational approximations have recently received a lot of attention and range from estimators of the fully factorized posterior, to the interpretation of Gaussian dropout as performing approximate inference with log-uniform priors and multiplicative Gaussian posteriors and facilitating a complex posterior using normalising flows. Since such Bayesian approaches often come at a high computational cost, alternative non-Bayesian approaches have been proposed, that can also account for predictive uncertainty. These include ensemble approaches, where smooth predictive estimates can be obtained by training ensembles of neural networks using adversarial examples, and evidential deep learning, where predictions of a NN are modelled as subjective opinions by placing a Dirichlet distribution on the class probabilities. Both for Bayesian and non-Bayesian approaches, uncertainty-awareness and the quality of predictive uncertainty are typically evaluated by analysing the behaviour of the predictive entropy for out-of-domain predictions in form of gradual perturbations (e.g. rotation of an image), adversarial examples or held-out classes. Notably, the focus of related work introduced above has been on image data and, thus, it remains unclear how these approaches perform for other data modalities, in particular when modelling sequences with long-range dependencies using complex architectures such as LSTMs or GRUs.

However, while an increasing predictive entropy for increasingly strong perturbations can be an indicator for uncertainty-awareness, simply high predictive entropy is not sufficient for trustworthy predictions, since this requires well-calibrated uncertainties, with the entropy matching the actual predictive power of the model. For example, if the entropy is too high, the model will yield under-confident predictions and similarly, if the entropy is too low, predictions will be over-confident. Thus, there still is a need for an efficient yet general modelling approach for obtaining well-calibrated, trustworthy probabilities for both in-domain samples as well as out-of-domain samples.

SUMMARY

In order to solve these problems in the state of the art the present invention provides a computer-implemented method of training a NN according to independent claim 1 as well as a corresponding computer program, computer-readable medium and data processing system according to the further independent claims. Refinements and embodiments are subject of the dependent claims.

A new training strategy is provided by the present invention combining conventional loss with an entropy-encouraging loss term and additionally or alternatively with an adversarial calibration loss term. This results in well-calibrated and technically trustworthy predictions for a wide range of perturbations and adversarial attacks. The present invention provides for an efficient yet general modelling approach for obtaining well-calibrated, trustworthy probabilities for both in-domain samples as well as out-of-domain samples that can readily be applied to a wide range of data modalities and model architectures including long-range dependencies using complex architectures such as LSTMs or GRUs.

According to a first aspect of the present invention a computer-implemented method of training a neural network (NN) comprises the steps receiving a training set and training the NN. In the step of receiving a training set, a training set T of training input data $X=(X_1, \ldots, X_n)$ and corresponding ground truth data $Y=(Y_1, \ldots, Y_n)$ for a predetermined number C of classes is received. Thereby, n is greater than one (n>1) and C is greater than or equal to one (C>=1). The step of training the NN comprises the iterative training steps selecting a training sub-set, generating current outputs, computing a categorical cross-entropy loss, computing a predictive entropy loss, computing a combined loss, checking whether the training converged, updating weights and stopping the training. In the training step of selecting a training sub-set, a training sub-set B of training input data $X_B$ and corresponding ground truth data $Y_B$ is selected from the training set T. Thereby, the cardinal number of the training sub-set is greater than zero and smaller than the cardinal number of the training set ($0<|B|<|T|$). In the training step of generating current outputs, current outputs of the NN for the sub-set B are generated by forward propagating the training input data $X_B$ of the training sub-set B in the NN. In the training step of computing a categorical cross-entropy loss, a categorical cross-entropy loss $L_{CCE}$ for the sub-set B is computed based on the current outputs and the corresponding ground truth data $Y_B$ of the training sub-set B. In the training step of computing a predictive entropy loss, a predictive entropy loss $L_S$ is computed by removing non-misleading evidence from the current outputs and distributing the remaining current outputs over the predetermined number C of classes. In the training step of computing a combined loss, a combined loss L is computed by adding to the categorical cross-entropy loss $L_{CCE}$ the predictive entropy loss $L_S$ weighted with a predetermined first loss factor $\lambda_S$. Thereby, the first loss factor $\lambda_S$ is greater than or equal to zero and smaller than or equal to 1 ($0<=\lambda_S<=1$). In the training step of checking whether the training converged, it is checked whether the training converged to a predefined lower limit for a convergence rate. In the step of updating weights, weights of the NN are updated based on the combined loss L and a predetermined training rate $\eta$, where the predetermined training rate $\eta$ is greater than zero and smaller than or equal to one ($0<\eta<=1$), in case the training did not converge. In the step of stopping the training, the training of the NN is stopped in case the training converged.

According to a second aspect of the present invention a computer-implemented method of training a NN comprises the steps receiving a training set and training the NN. In the step of receiving a training set, a training set T of training input data $X=(X_1, \ldots, X_n)$ and corresponding ground truth data $Y=(Y_1, \ldots, Y_n)$ for a predetermined number C of classes is received. Thereby, n is greater than one ($n>1$) and C is greater than or equal to one ($C>=1$). The step of training the NN comprises the iterative training steps selecting a training sub-set, generating current outputs, computing a categorical cross-entropy loss, sampling a perturbation level, generating an adversarial set, generating perturbed outputs, computing an adversarial calibration loss, checking whether the training converged, first time updating weights, second time updating the weights and stopping the training. In the training step of selecting a training sub-set, a training sub-set B of training input data $X_B$ and corresponding ground truth data $Y_B$ is selected from the training set T. Thereby, the cardinal number of the training sub-set is greater than zero and smaller than the cardinal number of the training set ($0<|B|<|T|$). In the training step of generating current outputs, current outputs of the NN for the sub-set B are generated by forward propagating the training input data $X_B$ of the training sub-set B in the NN. In the training step of computing a categorical cross-entropy loss, a categorical cross-entropy loss $L_{CCE}$ for the sub-set B is computed based on the current outputs and the corresponding ground truth data $Y_B$ of the training sub-set B. In the training step of sampling a perturbation level, a perturbation level $\varepsilon_B$ is randomly sampled with a value from 0 to 1. In the training step of generating an adversarial set, an adversarial set $B_{adv}$ of adversarial input data $X_{adv}$ is generated by applying a perturbation randomly selected from a predefined set of perturbations and weighted with the perturbation level $\varepsilon_B$ to the training input data $X_B$ of the training sub-set B. Thereby the cardinal number of the adversarial input data is equal to the cardinal number of the training input data of the training sub-set ($|X_{adv}|=|X_B|$). In the training step of generating perturbed outputs, perturbed outputs of the NN for the adversarial set $B_{adv}$ are generated by forward propagating the adversarial input data $X_{adv}$ of the adversarial set $B_{adv}$ in the NN. In the training step of computing an adversarial calibration loss, an adversarial calibration loss $L_{adv}$ is computed as the Euclidian norm ($L_2$ norm) of an expected calibration error ECE. The expected calibration error ECE takes a weighted average over the perturbed outputs grouped in a predefined number M of equally spaced bins each having an associated average confidence and accuracy. Thereby the predefined number M is greater than one ($M>1$). In the training step of checking whether the training converged, it is checked whether the training converged to a predefined lower limit for a convergence rate. In the step of first time updating weights, weights of the NN are updated first time based on the categorical cross-entropy loss $L_{CCE}$ and a predetermined training rate $\eta$, where the predetermined training rate $\eta$ is greater than zero and smaller than or equal to one ($0<\eta<=1$), in case the training did not converge. In the step of second time updating weights, weights of the NN are updated second time based on the adversarial calibration loss $L_{adv}$ weighted with a predetermined second loss factor $\lambda_{adv}$, where the predetermined second loss factor $\lambda_{adv}$ is greater than or equal to zero and smaller than or equal to one ($0<=\lambda_{adv}<=1$), and the predetermined training rate $\eta$, in case the training did not converge. In the step of stopping the training, the training of the NN is stopped in case the training converged.

According to a third aspect of the present invention a computer-implemented method of training a NN comprises the steps receiving a training set and training the NN. In the step of receiving a training set, a training set T of training input data $X=(X_1, \ldots, X_n)$ and corresponding ground truth data $Y=(Y_1, \ldots, Y_n)$ for a predetermined number C of classes is received. Thereby, n is greater than one ($n>1$) and C is greater than or equal to one ($C>=1$). The step of training the NN comprises the iterative training steps selecting a training sub-set, generating current outputs, computing a categorical cross-entropy loss, computing a predictive entropy loss, computing a combined loss, sampling a perturbation level, generating an adversarial set, generating perturbed outputs, computing an adversarial calibration loss, checking whether the training converged, first time updating weights, second time updating the weights and stopping the training. In the training step of selecting a training sub-set, a training sub-set B of training input data $X_B$ and corresponding ground truth data $Y_B$ is selected from the training set T. Thereby, the cardinal number of the training sub-set is greater than zero and smaller than the cardinal number of the training set ($0<|B|<|T|$). In the training step of generating current outputs, current outputs of the NN for the sub-set B are generated by forward propagating the training input data $X_B$ of the training sub-set B in the NN. In the training step of computing a categorical cross-entropy loss, a categorical cross-entropy loss $L_{CCE}$ for the sub-set B is computed based on the current outputs and the corresponding ground truth data $Y_B$ of the training sub-set B. In the training step of computing a predictive entropy loss, a predictive entropy loss $L_S$ is computed by removing non-misleading evidence from the current outputs and distributing the remaining current outputs over the predetermined number C of classes. In the training step of computing a combined loss, a combined loss L is computed by adding to the categorical cross-entropy loss $L_{CCE}$ the predictive entropy loss $L_S$ weighted with a predetermined first loss factor $\lambda_S$. Thereby, the first loss factor $\lambda_S$ is greater than or equal to zero and smaller than or equal to 1 ($0 <= \lambda_S <= 1$). In the training step of sampling a perturbation level, a perturbation level $\varepsilon_B$ is randomly sampled with a value from 0 to 1. In the training step of generating an adversarial set, an adversarial set $B_{adv}$ of adversarial input data $X_{adv}$ is generated by applying a perturbation randomly selected from a predefined set of perturbations and weighted with the perturbation level $\varepsilon_B$ to the training input data $X_B$ of the training sub-set B. Thereby the cardinal number of the adversarial input data is equal to the cardinal number of the training input data of the training sub-set ($|X_{adv}|=|X_B|$). In the training step of generating perturbed outputs, perturbed outputs of the NN for the adversarial set $B_{adv}$ are generated by forward propagating the adversarial input data $X_{adv}$ of the adversarial set $B_{adv}$ in the NN. In the training step of computing an adversarial calibration loss, an adversarial calibration loss $L_{adv}$ is computed as the Euclidian norm ($L_2$ norm) of an expected calibration error ECE. The expected calibration error ECE takes a weighted average over the perturbed outputs grouped in a predefined number M of equally spaced bins each having an associated average confidence and accuracy. Thereby the predefined number M is greater than one (M>1). In the training step of checking whether the training converged, it is checked whether the training converged to a predefined lower limit for a convergence rate.

In the step of first time updating weights, weights of the NN are updated first time based on based on the combined loss L and a predetermined training rate $\eta$, where the predetermined training rate $\eta$ is greater than zero and smaller than or equal to one ($0<\eta<=1$), in case the training did not converge. In the step of second time updating weights, weights of the NN are updated second time based on the adversarial calibration loss $L_{adv}$ weighted with a predetermined second loss factor $\lambda_{adv}$, where the predetermined second loss factor $\lambda_{adv}$ is greater than or equal to zero and smaller than or equal to one ($0<=\lambda_{adv}<=1$), and the predetermined training rate $\eta$, in case the training did not converge. In the step of stopping the training, the training of the NN is stopped in case the training converged.

According to a fourth aspect of the present invention a computer program comprises instructions which, when the program is executed by a computer, cause the computer to carry out the steps of the method according to any of the first, second or third aspect of the present invention.

According to a fifth aspect of the present invention a computer-readable medium has stored thereon the computer program according to the fourth aspect of the present invention.

According to a sixth aspect of the present invention a data processing system comprises means for carrying out the steps of the method according to any of the first, second or third aspect of the present invention.

According to a seventh aspect of the present invention a data processing system comprises a NN trained with the steps of the method according to any of the first, second or third aspect of the present invention.

The methods of training a NN according to the first, second and third aspect of the present invention all enable improved training of NNs by applying new loss terms in the training. The new loss terms account on the one hand for entropy (S) in training leading to technically trustworthy predictions and on the other hand for adversarial calibration in training leading to well-calibrated predictions. Thereby, the step of training of the method according to the third aspect of the present invention combines the training steps of the step of training of the method according to the first aspect of the present invention (predictive entropy loss $L_S$) with the training steps of the step of training of the method according to the second aspect of the present invention (adversarial calibration loss $L_{adv}$).

The NNs under training, in other words, the NNs that can be trained with the method of training according to the first, second and third aspect of the present invention and that may be comprised by the data processing system according to the seventh aspect of the present invention can be any NN.

The data processing system according to the seventh aspect of the present invention can implement the NN trained with the method according to any of the first, second or third aspect of the present invention or can comprise a data processing unit that implements said NN.

Artificial neural networks (ANN) or short neural networks (NN) are systems, in particular computing systems, inspired by biological neural networks that constitute animal brains. NNs "learn" to perform tasks by considering (labelled) examples called training data, generally without being designed with any task-specific rules. During an initial learning or training phase NNs automatically generate identifying characteristics from the (labelled) training data. NNs comprise a collection of connected nodes called artificial neurons, which loosely model the neurons in a biological brain. Each connection (synapses in the biological brain) can transmit a signal from one node to another. A node that receives a signal can process it and then signal to subsequent neurons connected to it. In common NN implementations, the signal at a connection between nodes is a real number (e.g. 0 . . . 1), and the output of each artificial neuron is computed by some non-linear function of the sum of its inputs (from other nodes). The connections between nodes are called "edges". The edges in NNs may each have a weight that is adjusted during training of the NNs. The weight increases or decreases the strength of the signal at the corresponding edge. Nodes may each have a threshold such that the signal is only sent if an aggregate signal exceeds that threshold. Typically, nodes are aggregated into layers. Different layers may perform different kinds of transformations on their inputs. Signals travel from a first layer or input layer to a last layer or output layer, possibly after traversing the layers multiple times.

In other words, an NN is a network of simple elements, the so called nodes or artificial neurons, which receive input. After receiving input the nodes change their internal state (activation) according to that input, and produce output depending on the input and activation. The network forms by connecting the output of certain nodes to the input of other nodes forming a directed, weighted graph. The weights as well as the functions that compute the activation of each node can be modified during initial learning/training, which is governed by a learning rule or paradigm.

A node/neuron receiving an input from at least one predecessor node/neuron consists of the following components: an activation, the node's state, depending on a discrete time parameter, optionally a threshold, which stays fixed unless changed by a learning/training function, an activation function (e.g. hyperbolic tangent function, sigmoid function, softmax function, rectifier function etc.) that computes the new activation at a given time and the net input and an output function computing the output from the activation (often the output function is the identity function). An important characteristic of the activation function is that it provides a smooth transition as input values change, i.e. a small change in input produces a small change in output.

An input node has no predecessor but serves as input interface for the whole NN. Similarly an output node has no successor and thus serves as output interface of the whole NN. An NN consists of edges/connections, each edge transferring the output of a node (predecessor) to the input of another, succeeding node (successor). Additionally to the assigned weight an edge may have a bias term added to a total weighted sum of inputs to serve as a threshold to shift the activation function. The propagation function computes the input to the succeeding node (successor) from the outputs of preceding nodes (predecessors) and may include the bias value.

A learning or training rule/paradigm is an algorithm which modifies the parameters of a respective NN in order for a given input to the NN to produce a favoured output. This training typically amounts to modifying the weights and/or thresholds of the variables within the NN. Given a specific task to solve and a class of functions, learning/training means using a set of observations (training input data of the training data) to find the one function of the class of functions, which solves the task in some optimal sense (corresponding labels or ground truth data of the training data). This entails defining a cost function or rather a loss function such that for the optimal solution the cost/loss is minimal and no other solution has a cost/loss less than the cost/loss of the optimal solution. The cost function or rather loss function is an important concept in learning/training, as it is a measure of how far away a particular solution is from an optimal solution to the problem to be solved. Learning/training algorithms search through the solution space to find a function that has the smallest possible cost/loss. For applications where the solution is data dependent, the cost/loss must necessarily be a function of the observations, otherwise the model would not relate to the data. It is frequently defined as a statistic to which only approximations can be made. It is possible to define an arbitrary cost function or rather loss function, however, a particular cost/loss function may be used either because it has desirable properties (e.g. convexity) or because it arises naturally from a particular formulation of the problem.

A NN can be discriminatively trained with a standard backpropagation algorithm. Backpropagation is a method to calculate the gradient of a loss function (produces the cost associated with a given state) with respect to the weights in the NN. The weight updates of backpropagation can be done via stochastic gradient descent. The choice of the loss function depends on factors such as the learning type (e.g. supervised, unsupervised, reinforcement etc.) and the activation function. Commonly, the activation function and loss function are the softmax function and cross-entropy function, respectively.

In other words, training a NN essentially means selecting one model from the set of allowed models (or, in a Bayesian framework, determining a distribution over the set of allowed models) that minimizes the cost or loss. Commonly some form of gradient descent is deployed, using backpropagation to compute the actual gradients. This is done by simply taking the derivative of the cost/loss function with respect to the network parameters and then changing those parameters in a gradient-related direction. Backpropagation training algorithms fall into three categories: steepest descent (with variable learning rate and momentum, resilient backpropagation), quasi-Newton (Broyden-Fletcher-Goldfarb-Shanno, one step secant), Levenberg-Marquardt and conjugate gradient (Fletcher-Reeves update, Polak-Ribiére update, Powell-Beale restart, scaled conjugate gradient).

Common training paradigms include supervised learning, unsupervised learning and reinforcement learning. Supervised learning uses a set of example pairs and the aim is to find a function in the allowed class of functions that matches the examples. In other words, the mapping implied by the data is inferred; the cost/loss function is related to the mismatch between the mapping of the NN and the data and it implicitly contains prior knowledge about the problem domain. The cost/loss may be the mean-squared error, which tries to minimize the average squared error between the NN's output and a target value over all the example pairs. Minimizing this cost/loss using gradient descent for the class of NNs called multilayer perceptrons (MLP), produces the backpropagation algorithm for training NNs. In unsupervised learning, some data is given and the cost/loss function to be minimized that can be any function of the data and the NN's output. The cost/loss function is dependent on the task and any a priori assumptions (e.g. implicit properties or parameters of the model, observed variables etc.). In reinforcement learning, data is usually not given, but generated by an agent's interactions with the environment. At each point in time the agent performs an action and the environment generates an observation and an instantaneous cost or loss according to some (usually unknown) dynamics. The aim is to discover a policy for selecting actions that minimizes some measure of a long-term cost/loss, e.g. the expected cumulative cost/loss. The environment's dynamics and the long-term cost/loss for each policy are usually unknown, but may also be estimated. The environment is commonly modelled as a Markov decision process (MDP) with states and actions with the following probability distributions: the instantaneous cost distribution, the observation distribution and the transition, while a policy is defined as the conditional distribution over actions given the observations. Taken together, the two then define a Markov chain (MC). The aim is to discover the policy (i.e., the MC) that minimizes the cost/loss.

The goal of training a NN is to optimize the weights and optionally other parameters of the NN such that the NN correctly maps input data provided at its input or rather input node(s) to output data at its output or rather output node(s). First, input data (one randomly selected sample of the training data set) is forward-propagated through the NN by providing the input data at the input of the NN. As a result of the forward-propagation a current output is computed by the NN based on the input data provided to the input node(s) and the internal weights of the NN. The current output is provided at the output node(s) of the NN. Then the current output is compared to the label or ground truth data of the training data set that is associated with the (randomly selected) input data. The comparison can be done by means of an error function or cost/loss function that computes an error/cost/loss. In order to archive training or learning the error/cost/loss is back-propagated by adapting the weights of the NN based on the computed error/cost/loss.

The received training set T comprises the input data X. The input data X comprises multiple samples of training input data $X_1$ to $X_n$. The training input data may be any kind of data that is used as basis for deduction of information by the NN.

The received training set T also comprises the corresponding ground truth data Y. The ground truth data Y comprises multiple samples of ground truth data $Y_1$ to $Y_n$ that corresponds to the respective samples of the training input data $X_1$ to $X_n$. The corresponding ground truth data gives the information that is to be deduced by the NN.

Each pair of sample of training input data and corresponding sample of ground truth data $X_1$, $Y_1$ to $X_n$, $Y_n$ belongs to one of the classes.

The ground truth data Y may be one-hot coded, where each output node of the NN corresponds to one of the bits of the one-hot code.

For example the samples of training input data $X_1$ to $X_n$ may be different images showing handwritten numbers and the corresponding samples of ground truth data $Y_1$ to $Y_n$ may be the respective number that is to be deduced by the NN. The classes may be C=10 classes where each class represents one number (0 to 9). Here the C=10 classes could be one-hot encoded in the following way:

0 corresponds to 1 0 0 0 0 0 0 0 0 0
1 corresponds to 0 1 0 0 0 0 0 0 0 0
2 corresponds to 0 0 1 0 0 0 0 0 0 0
3 corresponds to 0 0 0 1 0 0 0 0 0 0
4 corresponds to 0 0 0 0 1 0 0 0 0 0
5 corresponds to 0 0 0 0 0 1 0 0 0 0
6 corresponds to 0 0 0 0 0 0 1 0 0 0
7 corresponds to 0 0 0 0 0 0 0 1 0 0
8 corresponds to 0 0 0 0 0 0 0 0 1 0
9 corresponds to 0 0 0 0 0 0 0 0 0 1

As another example, the samples of training input data $X_1$ to $X_n$ may be different medical image data like Magnetic Resonance images, Computer Tomography images, Sonography images etc. and the corresponding samples of ground truth data $Y_1$ to $Y_n$ may be respective maps where each pixel or voxel of the medical image data is assigned a different type of tissue or organ that is to be deduced by the NN. The classes may be C=3 classes where each class represents one type of tissue. Here the C=3 classes could be one-hot encoded in the following way:

normal tissue corresponds to 1 0 0
tumorous tissue corresponds to 0 1 0
fibrous tissue corresponds to 0 0 1

Alternatively, the classes may be C=4 classes where each class represents one type of organ. Here the C=4 classes could be one-hot encoded in the following way:

lung tissue corresponds to 1 0 0 0
heart tissue corresponds to 0 1 0 0
bone corresponds to 0 0 1 0
other tissue corresponds to 0 0 0 1

As another example, the samples of training input data $X_1$ to $X_n$ may be data of varying courses of different physical quantities like force, temperature, speed etc. and the corresponding samples of ground truth data $Y_1$ to $Y_n$ may be respective state of a machine that is to be deduced by the NN. The classes may be C=3 classes where each class represents one state of the machine. Here the C=3 classes could be one-hot encoded in the following way:

normal operation corresponds to 1 0 0
start-up phase corresponds to 0 1 0
failure corresponds to 0 0 1

As another example, the samples of training input data $X_1$ to $X_n$ may be texts regarding different topics like politics, sports, economics, science etc. and the corresponding samples of ground truth data $Y_1$ to $Y_n$ may be the respective topic that is to be deduced by the NN. The classes may be C=4 classes where each class represents one state of the machine. Here the C=4 classes could be one-hot encoded in the following way:

politics corresponds to 1 0 0 0
sports corresponds to 0 1 0 0
economics corresponds to 0 0 1 0
science corresponds to 0 0 0 1

But any other type of input data and any other type of information to be deduced by the NN can be used for training the NN.

The iterative training steps of the step of training are iteratively executed until the training converges. Thereto, the rate of training is compared to the predefined lower threshold for the rate of training. In other words, when the last adjustment of the weights of the NN did not improve the output of the NN more than predefined as lower threshold, then the training is aborted.

First, there is selected the training sub-set B in the training step of selecting a training sub-set. Thereto, a sub-set of the training input data X and a corresponding sub-set of the ground truth data Y is selected for the current iteration of the step of training. The training sub-set B may be randomly selected. The number of samples of training input data $X_i$ selected as the training input data $X_B$ of the training sub-set B and accordingly the number of corresponding samples of ground truth data $Y_i$ of the ground truth data $Y_B$ of the training sub-set B and, thus, the cardinal number of the training sub-set B are predefined.

In the training step of generating current outputs, the selected training input data $X_B$ is provided to the input nodes (at least one) of the NN and forward-propagated in the NN. Thereby, the information contained in the training input data $X_B$ is forwarded through the layers (at least one) of the NN where each node of the layers of the NN has a current weight. Based on the current weights, the training input data $X_B$ is computed into the current outputs at the output nodes (at least one) of the NN.

In the training step of computing a categorical cross-entropy loss, the generated current outputs are compared to the corresponding ground truth data $Y_B$ of the training sub-set B in order to compute the categorical cross-entropy loss $L_{CCE}$.

In the training step of computing a predictive entropy loss, first non-misleading evidence is removed from the current outputs. Non-misleading evidence is an output generated by the NN, where the probability of one class is set to one and all other probabilities of the remaining classes are set to zero. In other words, non-misleading evidence is a "perfect" prediction made by the NN, where the NN has unambiguously identified one class for the respective sample of training input data. The remaining (misleading) current outputs are then distributed over the predetermined number C of classes in order to calculate the predictive entropy loss $L_S$. The predictive entropy loss $L_S$ may be calculated by the following formula:

$$L_S = \sum_{i=1}^{n} \sum_{j=1}^{C} -\frac{1}{C} \log(p_{ij}(1 - y_{ij}) + y_{ij})$$

where $p_{ij}$ is the confidence associated with to the jth class of sample i and $y_{ij}$ is its one-hot encoded label.

Based on the calculated categorical cross-entropy loss $L_{CCE}$ and on the calculated predictive entropy loss $L_S$ the combined loss L is calculated in the training step of computing a combined loss. Thereto, to the categorical cross-entropy loss $L_{CCE}$ the predictive entropy loss $L_S$ that is weighted with the predetermined first loss factor $\lambda_S$ is added. The combined loss L may be calculated by the following formula:

$$L = L_{CCE} + \lambda_S L_S$$

In the training step of sampling a perturbation level, the perturbation level $\varepsilon_B$ is randomly sampled such that it takes a value greater than zero and lower than or equal to one ($0 < \varepsilon_B \leq 1$).

Then the adversarial set $B_{adv}$ is generated in the training step of generating an adversarial set. First, a perturbation (e.g. a rotation or shift of a training input image or a word replacement in a training input text etc.) is randomly selected from a predefined set of perturbations. Then the selected perturbation is weighted with the perturbation level $\varepsilon_B$ and applied to the training input data $X_B$ of the training sub-set B, which are thereby transformed into the adversarial input data $X_{adv}$ of the adversarial set $B_{adv}$. Consequently, the cardinal number of the adversarial input data $X_{adv}$ (and also of the adversarial set $B_{adv}$) is equal to the cardinal number of the training input data $X_B$ of the training sub-set B.

Based on the adversarial input data $X_{adv}$ the perturbed outputs are generated at the output nodes of the NN in the training step of generating perturbed outputs. Thereto, the adversarial input data $X_{adv}$ is forward-propagated through the layers (at least one) of the NN where each node of the layers of the NN has a current weight. Based on the current weights, the adversarial input data $X_{adv}$ is computed into the perturbed outputs at the output nodes (at least one) of the NN.

In the training step of computing an adversarial calibration loss, the $L_2$ norm of the expected calibration error ECE is calculated as the adversarial calibration loss $L_{adv}$. The expected calibration error ECE takes a weighted average over the perturbed outputs, which perturbed outputs are grouped in the predefined number M of equally spaced bins. Each bin has an associated average confidence and accuracy. For example, the perturbed outputs may be grouped into M=10 bins, where each bin covers a confidence interval $I_m$ of size 0.1:

first bin confidence interval $I_m$ between 0 and 0.1
second bin confidence interval $I_m$ between 0.1 and 0.2
third bin confidence interval $I_m$ between 0.2 and 0.3
fourth bin confidence interval $I_m$ between 0.3 and 0.4
fifth bin confidence interval $I_m$ between 0.4 and 0.5
sixth bin confidence interval $I_m$ between 0.5 and 0.6
seventh bin confidence interval $I_m$ between 0.6 and 0.7
eighth bin confidence interval $I_m$ between 0.7 and 0.8
ninth bin confidence interval $I_m$ between 0.8 and 0.9
tenth bin confidence interval $I_m$ between 0.9 and 1

The expected calibration error ECE may be calculated by the following formula:

$$ECE = \sum_{m=1}^{M} \frac{|B_m|}{n} |acc(B_m) - conf(B_m)|$$

where $B_m$ is a set of indices of samples whose prediction confidence falls into the associated confidence interval $I_m$, $conf(B_m)$ is the average confidence associated to $B_m$ and $acc(B_m)$ is the accuracy associated to $B_m$.

The adversarial calibration loss $L_{adv}$ may be calculated by the following formula:

$$L_{adv} = \|ECE\|_2 = \left\| \sum_{m=1}^{M} \frac{|B_m|}{n} |acc(B_m) - conf(B_m)| \right\|_2$$

When the training did not converge and the training of the NN is not stopped, the weights of the NN are adapted based on the computed losses.

In the method according to the first aspect of the present invention, the weights of the NN are adapted in the training step of updating the weights by updating the weights based on the combined loss L. Thereto, the combined loss L is back-propagated to the weights of the NN by changing the weights according to the combined loss L. It is determined how much each weight contributes to the combined loss L and then each weight is changed proportionally to its contribution to the combined loss L.

Likewise, in the method according to the third aspect of the present invention, the weights of the NN are adapted in the training step of first time updating the weights by updating the weights first time based on the combined loss L. Thereto, the combined loss L is back-propagated to the weights of the NN by changing the weights according to the combined loss L. It is determined how much each weight contributes to the combined loss L and then each weight is changed proportionally to its contribution to the combined loss L.

In the method according to the second aspect of the present invention, the weights of the NN are adapted in the training step of first time updating the weights by updating the weights first time only based on the categorical cross entropy loss $L_{CCE}$. Thereto, the categorical cross entropy loss $L_{CCE}$ is back-propagated to the weights of the NN by changing the weights according to the categorical cross entropy loss $L_{CCE}$. It is determined how much each weight contributes to the categorical cross entropy loss $L_{CCE}$ and then each weight is changed proportionally to its contribution to the categorical cross entropy loss $L_{CCE}$.

Further, in the method according to the second and third aspect the weights are adapted a second time. In the training step of second time updating the weights of the NN are updated second time based on the adversarial calibration loss $L_{adv}$. Thereto, the adversarial calibration loss $L_{adv}$ is weighted with the second loss factor $\lambda_{adv}$ and back-propagated to the weights of the NN by changing the weights according to the weighted adversarial calibration loss $L_{adv}$. It is determined how much each weight contributes to the adversarial calibration loss $L_{adv}$ and then each weight is changed proportionally to its contribution to the categorical cross entropy loss $L_{CCE}$ weighted with the second loss factor $\lambda_{adv}$.

In all the training steps of updating weights, i.e. the step of updating weights of the method according to the first aspect of the present invention, the step of first time updating weights of the method according to the second and third aspect of the present invention and the step of second time updating weights of the method according to the second and third aspect of the present invention, the amount of adapting the weights may be controlled with the predetermined training rate $\eta$. In particular, each weight of the NN may be adjusted in the respective step of updating weights by the following formula:

$$w_l^{updated} = w_l^{current} - \eta \frac{\partial L_{-/CCE/adv}}{\partial w_l^{current}}$$

where $w_l^{current}$ is the current value of the lth weight of the NN, $w_l^{updated}$ is the updated or adjusted value of the lth weight of the NN, $L_{-/CCE/adv}$ is the associated loss (either L or $L_{CCE}$ or $L_{adv}$) depending on the respective step of updating weights and $$\frac{\partial L_{-/CCE/adv}}{\partial w_l^{current}}$$

is the partial derivative of the associated loss $L_{\_/CCE/adv}$ with respect to the lth weight of the NN.

The approach for training a NN according to the first, second and third aspect of the present invention is simple and general, requiring only a small modification of existing training procedures. Further, the methods according to the first, second and third aspect of the present invention provide for well-calibrated and technically trustworthy predictions for a wide range of perturbations and adversarial attacks.

A NN trained with the method according to any of the first, second and third aspect of the present invention consumes input data of the same domain (same size and type of value) as the training input data X of the training set T and produces outputs of the same domain as the ground truth data Y of the training set T. The data processing unit according to the seventh aspect of the present invention may provide such input data to the trained NN and receive the outputs generated or derived by the NN based on the provided input data. The received outputs may be stored in a storage of the data processing system and/or displayed to a user via a monitor or printout by the data processing system.

According to a refinement of the present invention the perturbation level $\varepsilon_B$ is randomly sampled from a perturbation level set $\varepsilon$. The perturbation level set $\varepsilon$ includes a predefined number of values from 0 to 1. Preferably, the perturbation level set $\varepsilon$ includes a predefined number of values from 0 to 0.5. Most preferably, the perturbation level set $\varepsilon$ includes the values 0, 0.05, 0.1, 0.15, 0.2, 0.25, 0.3, 0.35, 0.4, 0.45.

According to a refinement of the present invention the predefined set of perturbations includes image-based perturbation types or word-based perturbation types.

The image-based perturbation types may include left rotation, right rotation, shift in x direction, shift in y direction, xy shift, shear, zoom in x direction, zoom in y direction and xy zoom for image data as training input data X of the training set T. The perturbation level $\varepsilon_B$ sets how much the perturbation is applied (e.g. rotation by what angle (0 corresponds to 0° and 1 corresponds to 180° or π), shift or shear by what length (e.g. 0 corresponds to no shift/shear and 1 corresponds to shift/shear by 50%), zoom by what factor (e.g. 0 corresponds to 100% and 1 corresponds to 200%) or the like).

The word-based perturbation types may include a perturbation that is generated by first drawing a random set of words in a corpus. Next each of these words is replaced by a word drawn at random from a vocabulary. The perturbation level $\varepsilon_B$ sets how much the perturbation is applied (replacement by how many words of the corpus with random words of the vocabulary (e.g. 0 corresponds to no replacement and 1 corresponds to 100% of the words) or the like).

According to a refinement of the present invention the method further comprises the subsequent step of evaluating a robustness of the trained NN. The subsequent step of evaluating comprises the sub-steps providing the trained NN with a first set, generating perturbed outputs, computing the ECEs for the respective generated outputs, providing the trained NN with at least one further set of multiple perturbed input datasets, generating perturbed outputs of the NN based on the provided at least one further set of multiple perturbed input datasets, computing the ECEs for the respective generated outputs and calculating micro-averaged ECEs. In the sub-step of providing the trained NN with a first set, the NN is provided with a first set of multiple perturbed input datasets. The multiple perturbed input datasets have been perturbed with a perturbation of a first perturbation-type. Thereby, each input dataset has been perturbed with a different predefined perturbation level $\varepsilon_B$. In the sub-step of generating perturbed outputs of the NN, perturbed outputs of the NN are generated based on the provided first set multiple perturbed input datasets. In the step of computing the ECEs for the respective generated outputs, the ECEs are computed for the respective generated outputs. In the step of providing the trained NN with at least one further set of multiple perturbed input datasets, the trained NN is provided with at least one further set of multiple perturbed input datasets. The multiple perturbed input datasets have been perturbed with a perturbation of at least one further perturbation-type. Thereby, each input dataset has been perturbed with a different predefined perturbation level $\varepsilon_B$. In the sub-step of generating perturbed outputs of the NN based on the provided at least one further set of multiple perturbed input datasets, perturbed outputs of the NN are generated based on the provided at least one further set of multiple perturbed input datasets. In the step of computing the ECEs for the respective generated outputs, the ECEs are computed for the respective generated outputs. In the step of calculating micro-averaged ECEs, micro-averaged ECEs are calculated across the generated outputs of each provided set of multiple perturbed input datasets by calculating the average of the respective ECEs.

After the step of training has been stopped and training aborted, the NN is trained. The performance regarding trustworthiness or robustness of the trained NN can be evaluated with the step of evaluating a robustness of the trained NN.

In the sub-step of providing the trained NN with a first set, the trained NN is provided with the multiple perturbed input datasets of the first set. The perturbed input datasets of the first set have been generated by weighting the perturbation of the first perturbation-type with a different one of the predefined levels of perturbation $\varepsilon_B$ for each input dataset and then applying the accordingly weighted perturbation of the first perturbation-type to the respective input datasets.

The perturbed outputs are generated in the sub-step of generating perturbed outputs by forward-propagating the multiple perturbed input datasets of the first set through the layers (at least one) of the trained NN where each node of the layers of the NN has a trained weight. Based on the trained weights, the perturbed input datasets are computed into the perturbed outputs at the output nodes (at least one) of the NN.

In the step of computing the ECEs for the respective generated outputs, the expected calibration errors ECEs are calculated for the respective generated outputs in the same way as described above for the outputs during the step of training.

Then, the NN is provided with the multiple perturbed input datasets of the at least one further set. The perturbed input datasets of the at least one further set have been generated by weighting the perturbation of the at least one further perturbation-type with a different one of the predefined levels of perturbation $\varepsilon_B$ for each input dataset and then applying the accordingly weighted perturbation of the at least one further perturbation-type to the respective input datasets.

The perturbed outputs are generated in the sub-step of generating perturbed outputs of the NN based on the provided at least one further set of multiple perturbed input datasets by forward-propagating the multiple perturbed input datasets of the at least one further set through the layers (at least one) of the trained NN where each node of the layers of the NN has the trained weight. Based on the trained weights, the perturbed input datasets are computed into the perturbed outputs for the at least one further set at the output nodes (at least one) of the NN.

In the step of computing the ECEs for the respective generated outputs, the expected calibration errors ECEs are calculated for the respective generated outputs in the same way as described above for the outputs during the step of training.

Finally, in the step of calculating micro-averaged ECEs across the generated outputs of each provided set of multiple perturbed input datasets, micro-averaged ECEs are calculated across the generated outputs of each provided set of multiple perturbed input datasets by calculating the average of the respective ECEs. The micro-averaged ECEs are the mean values of the ECEs of the generated outputs associated with one type of perturbation over different perturbation levels $\varepsilon_B$. The micro-averaged ECEs enable a detailed assessment of the trustworthiness or rather robustness of the predictions of the trained NN

BRIEF DESCRIPTION

The present invention and its technical field are subsequently explained in further detail by exemplary embodiments shown in the drawings. The exemplary embodiments only conduces better understanding of the present invention and in no case are to be construed as limiting for the scope of the present invention. Particularly, it is possible to extract aspects of the subject-matter described in the figures and to combine it with other components and findings of the present description or figures, if not explicitly described differently. Equal reference signs refer to the same objects, such that explanations from other figures may be supplementally used.

DETAILED DESCRIPTION

Figure 1:
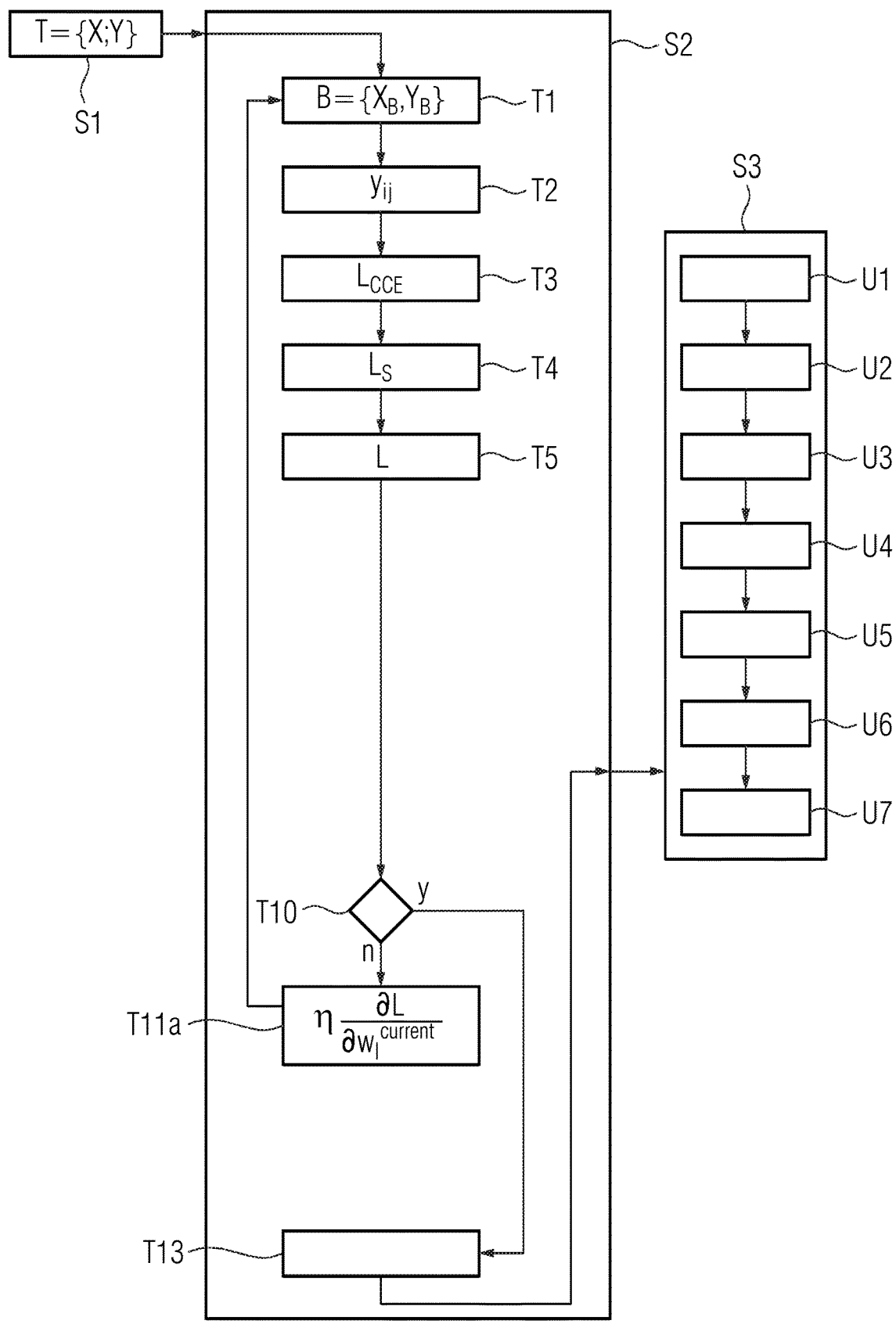
FIG. 1 shows a schematic flow chart of the method of training a NN according to the first aspect of the present invention.

In FIG. 1 the method of training a NN according to the first aspect of the present invention is schematically depicted. The method comprises the steps receiving S1 a training set, training S2 the NN and optionally evaluating S3 a robustness of the trained NN.

In the step of receiving S1 a training set, exemplarily a training set T={X; Y} of training input data X=($X_1$, ..., $X_{1000}$) that are hand written images of numbers from 0 to 9 and corresponding ground truth data Y=($Y_1$, ..., $Y_{1000}$) that are the corresponding numbers for the ten classes (C=10) that resemble the possible numbers from 0 to 9 is received.

Here the C=10 classes are one-hot encoded in the following way:
0 corresponds to 1 0 0 0 0 0 0 0 0 0
1 corresponds to 0 1 0 0 0 0 0 0 0 0
2 corresponds to 0 0 1 0 0 0 0 0 0 0
3 corresponds to 0 0 0 1 0 0 0 0 0 0
4 corresponds to 0 0 0 0 1 0 0 0 0 0
5 corresponds to 0 0 0 0 0 1 0 0 0 0
6 corresponds to 0 0 0 0 0 0 1 0 0 0
7 corresponds to 0 0 0 0 0 0 0 1 0 0
8 corresponds to 0 0 0 0 0 0 0 0 1 0
9 corresponds to 0 0 0 0 0 0 0 0 0 1

The step of training S2 the NN comprises the iterative training steps selecting T1 a training sub-set, generating T2 current outputs, computing T3 a categorical cross-entropy loss, computing T4 a predictive entropy loss, computing T5 a combined loss, checking T10 whether the training converged, updating T11a weights and stopping T13 the training.

In the training step of selecting T1 a training sub-set, exemplarily a training sub-set B={$X_B$; $Y_B$} of training input data $X_B$=($X_{B,1}$, ..., $X_{B,100}$) that are 100 randomly selected images from the training set T and corresponding ground truth data $Y_B$=($Y_{B,1}$, ..., $Y_{B,100}$) that are the corresponding numbers is randomly selected from the training set T.

In the training step of generating T2 current outputs, current outputs $y_{ij}$ of the NN for the sub-set B are generated by forward propagating the exemplarily 100 images of the training input data $X_B$ of the training sub-set B in the NN.

In the training step of computing T3 a categorical cross-entropy loss, a categorical cross-entropy loss $L_{CCE}$ for the sub-set B is computed based on the current outputs $y_{ij}$ and the corresponding ground truth data $Y_B$ of the training sub-set B.

In the training step of computing T4 a predictive entropy loss, a predictive entropy loss $L_S$ is computed. Thereto, non-misleading evidence (probability of one class is set to one and all other probabilities of the remaining classes are set to zero) is removed from the current outputs $y_{ij}$. The remaining current outputs $y_{ij}$ are then distributed over the ten classes in order to calculate the predictive entropy loss $L_S$. The predictive entropy loss $L_S$ is calculated by the following formula:

$$L_S = \sum_{i=1}^{n} \sum_{j=1}^{C} -\frac{1}{C} \log(p_{ij}(1 - y_{ij}) + y_{ij})$$

where $p_{ij}$ is the confidence associated with to the jth class of sample i and $y_{ij}$ is its one-hot encoded label.

In the training step of computing T5 a combined loss, a combined loss L is computed by adding to the categorical cross-entropy loss $L_{CCE}$ the predictive entropy loss $L_S$ weighted with a predetermined first loss factor $\lambda_S$ of exemplarily 0.5.

The combined loss L may be calculated by the following formula:

$$L = L_{CCE} + \lambda_S L_S$$

In the training step of checking T10 whether the training converged, it is checked whether the training converged to a predefined lower limit for a convergence rate.

In the step of updating T11a weights, weights $w_l$ of the NN are updated based on the combined loss L and a predetermined training rate η of exemplarily 0.2 in case the training did not converge. Thereto, the combined loss L is back-propagated to the weights $w_l$ of the NN by changing the weights according to the combined loss L. It is determined how much each weight $w_l$ contributes to the combined loss L and then each weight $w_l$ is changed proportionally to its contribution to the combined loss L. Each weight $w_l$ of the NN may be adjusted in the respective step of updating weights by the following formula:

$$w_l^{updated} = w_l^{current} - \eta \frac{\partial L}{\partial w_l^{current}}$$

where $w_l^{current}$ is the current value of the lth weight of the NN, $w_l^{updated}$ is the updated or adjusted value of the lth weight of the NN and $$\frac{\partial L}{\partial w_l^{current}}$$

is the partial derivative of the combined loss L with respect to the lth weight of the NN.

In the step of stopping T13 the training, the training of the NN is stopped in case the training converged.

After the training has converged and the iteration of the step of training S2 the NN is aborted, the NN is completely trained. Optionally, the trained NN can be evaluated in the optional step of evaluating S3 a robustness of the trained NN that comprises the sub-steps providing U1 the trained NN with a first set, generating U2 perturbed outputs, computing U3 the ECEs for the respective generated outputs, providing U4 the trained NN with at least one further set of multiple perturbed input datasets, generating U5 perturbed outputs of the NN based on the provided at least one further set of multiple perturbed input datasets, computing U6 the ECEs for the respective generated outputs and calculating U7 micro-averaged ECEs.

In the sub-step of providing U1 the trained NN with a first set, the NN is provided with a first set of multiple perturbed input datasets. The multiple perturbed input datasets have been perturbed with a perturbation of a first perturbation-type. Thereby, each input dataset has been perturbed with a different predefined perturbation level $\varepsilon_B$.

In the sub-step of generating U2 perturbed outputs of the NN, perturbed outputs of the NN are generated based on the provided first set multiple perturbed input datasets.

In the sub-step of computing U3 the ECEs for the respective generated outputs, the ECEs are computed for the respective generated outputs. The expected calibration errors ECEs are calculated for the respective generated outputs in the same way as described above for the outputs during the step of training S2 the NN.

In the sub-step of providing U4 the trained NN with at least one further set of multiple perturbed input datasets, the trained NN is provided with at least one further set of multiple perturbed input datasets. The multiple perturbed input datasets have been perturbed with a perturbation of at least one further perturbation-type. Thereby, each input dataset has been perturbed with a different predefined perturbation level $\varepsilon_B$.

In the sub-step of generating U5 perturbed outputs of the NN based on the provided at least one further set of multiple perturbed input datasets, perturbed outputs of the NN are generated based on the provided at least one further set of multiple perturbed input datasets.

In the sub-step of computing U6 the ECEs for the respective generated outputs, the ECEs are computed for the respective generated outputs. The expected calibration errors ECEs are calculated for the respective generated outputs in the same way as described above for the outputs during the step of training S2 the NN.

In the sub-step of calculating U7 micro-averaged ECEs, micro-averaged ECEs are calculated across the generated outputs of each provided set of multiple perturbed input datasets by calculating the average of the respective ECEs. The micro-averaged ECEs enable a detailed assessment of the trustworthiness or rather robustness of the predictions of the trained NN.

Figure 2:
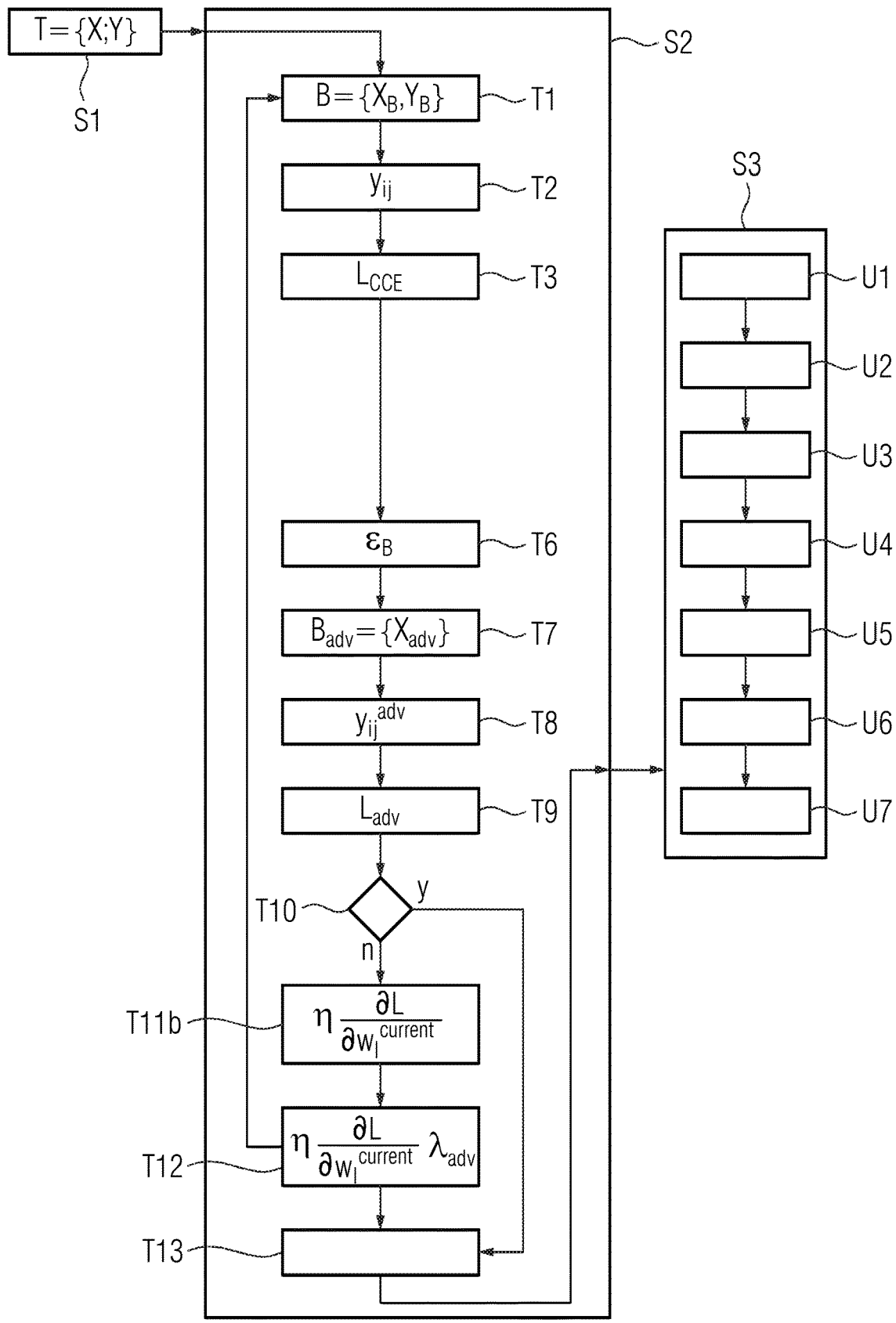
FIG. 2 shows a schematic flow chart of the method of training a NN according to the second aspect of the present invention.

In FIG. 2 the method of training a NN according to the second aspect of the present invention is schematically depicted. The method according to the second aspect of the present invention and as depicted in FIG. 2 is similar to the method according to the first aspect of the present invention and as depicted in FIG. 1. Therefore, only differences between the two will be described in the following. The step of training S2 the NN of the method of FIG. 2 comprises the training steps sampling T6 a perturbation level, generating T7 an adversarial set, generating T8 perturbed outputs, computing T9 an adversarial calibration loss first time updating T11b weights and second time updating T12 the weights instead of the steps computing T4 a predictive entropy loss, computing T5 a combined loss and updating T11a weights of the step of training S2 the NN of the method of FIG. 1.

In the training step of sampling T6 a perturbation level, a perturbation level $\varepsilon_B$ is randomly sampled from the exemplary set F that includes the values 0, 0.05, 0.1, 0.15, 0.2, 0.25, 0.3, 0.35, 0.4, 0.45.

In the training step of generating T7 an adversarial set, an adversarial set $B_{adv}$ of adversarial input data $X_{adv}$ is generated. Thereto, a perturbation is randomly selected from a predefined set of perturbations that exemplarily includes the image-based perturbation types left rotation, right rotation, shift in x direction, shift in y direction, xy shift, shear, zoom in x direction, zoom in y direction and xy zoom. Then the selected perturbation is weighted with the sampled perturbation level $\varepsilon_B$ and applied to the training input data $X_B$ of the training sub-set B. Thereby, the training input data that is to be perturbed (i.e. respective images of a number) is transformed into the adversarial input data $X_{adv}$ (perturbed handwritten images of a number) of the adversarial set $B_{adv}$.

In the training step of generating T8 perturbed outputs, perturbed outputs of the NN for the adversarial set $B_{adv}$ are generated by forward propagating the exemplarily 100 perturbed images as the adversarial input data $X_{adv}$ of the adversarial set $B_{adv}$ in the NN.

In the training step of computing T9 an adversarial calibration loss, an adversarial calibration loss $L_{adv}$ is computed as the Euclidian norm ($L_2$ norm) of an expected calibration error ECE. Thereto, the perturbed outputs are grouped into exemplarily M=10 bins, where each bin covers a confidence interval $I_m$ of size 0.1:

first bin confidence interval $I_m$ between 0 and 0.1
second bin confidence interval $I_m$ between 0.1 and 0.2
third bin confidence interval $I_m$ between 0.2 and 0.3
fourth bin confidence interval $I_m$ between 0.3 and 0.4
fifth bin confidence interval $I_m$ between 0.4 and 0.5
sixth bin confidence interval $I_m$ between 0.5 and 0.6
seventh bin confidence interval $I_m$ between 0.6 and 0.7
eighth bin confidence interval $I_m$ between 0.7 and 0.8
ninth bin confidence interval $I_m$ between 0.8 and 0.9
tenth bin confidence interval $I_m$ between 0.9 and 1

The expected calibration error ECE is calculated by the following formula:

$$ECE = \sum_{m=1}^{M} \frac{|B_m|}{n} |acc(B_m) - conf(B_m)|$$

where $B_m$ is a set of indices of samples whose prediction confidence falls into the associated confidence interval $I_m$, $conf(B_m)$ is the average confidence associated to $B_m$ and $acc(B_m)$ is the accuracy associated to B.

The adversarial calibration loss $L_{adv}$ is calculated by the following formula:

$$L_{adv} = \|ECE\|_2 = \left\| \sum_{m=1}^{M} \frac{|B_m|}{n} |acc(B_m) - conf(B_m)| \right\|_2$$

In the step of first time updating T11b weights, weights $w_l$ of the NN are updated first time based on the categorical cross-entropy loss $L_{CCE}$ and the predetermined training rate η in case the training did not converge.

In the step of second time updating T12 weights, weights of the NN are updated second time based on the adversarial calibration loss $L_{adv}$ weighted with a predetermined second loss factor $\lambda_{adv}$ of exemplarily 0.5 and the predetermined training rate η, in case the training did not converge.

Figure 3:
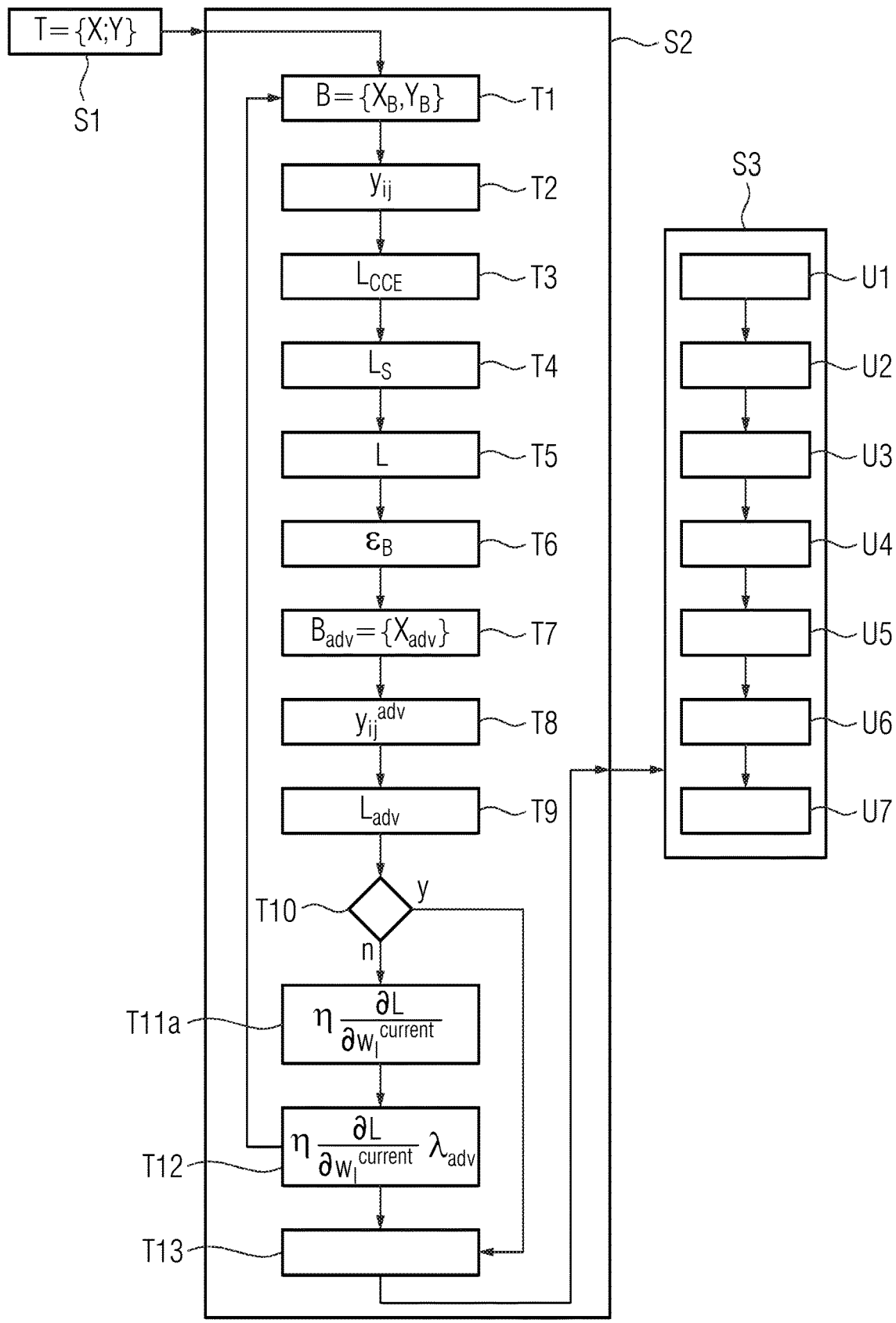
FIG. 3 shows a schematic flow chart of the method of training a NN according to the third aspect of the present invention.

In FIG. 3 the method of training a NN according to the third aspect of the present invention is schematically depicted. The method according to the third aspect of the present invention and as depicted in FIG. 3 is similar to the methods according to the first and second aspects of the present invention and as depicted in FIGS. 1 and 2. Therefore, only differences between the three will be mentioned in the following. The step of training S2 the NN of the method of FIG. 3 comprises the training steps T1 to T3, T10 and T13 of the step of training S2 the NN of the methods of FIGS. 1 and 2. Further, the step of training S2 the NN of the method of FIG. 3 comprises the training steps T4 and T5 of the step of training S2 the NN of the method of FIG. 1. Also, the training step of updating T11a weights of the step of training S2 the NN of the method of FIG. 1 is comprised by the step of training S2 the NN of the method of FIG. 3 as the training step first time updating T11a weights. Additionally, the step of training S2 the NN of the method of FIG. 3 comprises the training steps T6 to T9 and second time updating T12 of the step of training S2 the NN of the method of FIG. 2. Consequently, the method of FIG. 3 combines in its step of training S2 the training steps of the steps of training S2 of the methods of FIGS. 1 and 2.

The computer program according to the fourth aspect of the present invention may comprise instructions which, when the program is executed by a computer, cause the computer to carry out the steps S1 to S3 including the respective training steps T1 to T3 and sub-steps U1 to U7 of the method according to any of the first, second and third aspect of the present invention and as depicted in FIGS. 1 to 3.

Figure 4:
FIG. 4 shows a schematic view of the computer-readable medium according to the fifth aspect of the present invention.

In FIG. 4 an embodiment of the computer-readable medium 20 according to the fifth aspect of the present invention is schematically depicted.

Here, exemplarily a computer-readable storage disc 20 like a Compact Disc (CD), Digital Video Disc (DVD), High Definition DVD (HD DVD) or Blu-ray Disc (BD) has stored thereon the computer program according to the fourth aspect of the present invention and as schematically shown in FIGS. 1 to 3. However, the computer-readable medium may also be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Tesa tape, Laserdisc, Phasewriter (Phasewriter Dual, PD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)), a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM).

Figure 5:
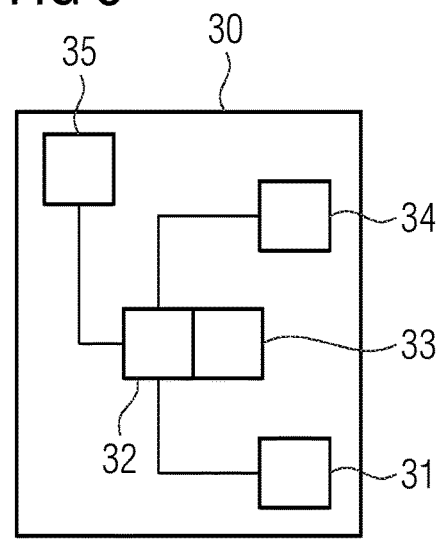
FIG. 5 shows a schematic view of the data processing system according to the sixth aspect of the present invention.

In FIG. 5 an embodiment of the data processing system 30 according to the sixth aspect of the present invention is schematically depicted.

The data processing system 30 may be a personal computer (PC), a laptop, a tablet, a server, a distributed system (e.g. cloud system) and the like. The data processing system 30 comprises a central processing unit (CPU) 31, a memory having a random access memory (RAM) 32 and a non-volatile memory (MEM, e.g. hard disk) 33, a human interface device (HID, e.g. keyboard, mouse, touchscreen etc.) 34 and an output device (MON, e.g. monitor, printer, speaker, etc.) 35. The CPU 31, RAM 32, HID 34 and MON 35 are communicatively connected via a data bus. The RAM 32 and MEM 33 are communicatively connected via another data bus. The computer program according to the fourth aspect of the present invention and schematically depicted in FIGS. 1 to 3 can be loaded into the RAM 32 from the MEM 33 or another computer-readable medium 20. According to the computer program the CPU 31 executes the steps S1 to S3 including the respective training steps T1 to T3 and sub-steps U1 to U7 of the computer-implemented method according to any of the first, second and third aspect of the present invention and as schematically depicted in FIGS. 1 to 3. The execution can be initiated and controlled by a user via the HID 34. The status and/or result of the executed computer program may be indicated to the user by the MON 35. The result of the executed computer program may be permanently stored on the non-volatile MEM 33 or another computer-readable medium.

In particular, the CPU 31 and RAM 32 for executing the computer program may comprise several CPUs 31 and several RAMs 32 for example in a computation cluster or a cloud system. The HID 34 and MON 35 for controlling execution of the computer program may be comprised by a different data processing system like a terminal communicatively connected to the data processing system 30 (e.g. cloud system).

Figure 6:
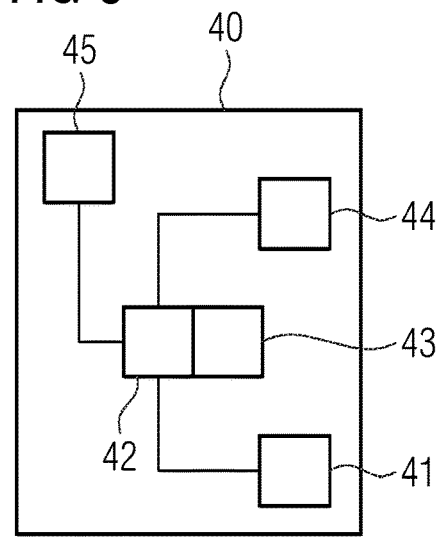
FIG. 6 shows a schematic view of the data processing system according to the seventh aspect of the present invention.

In FIG. 6 an embodiment of the data processing system 40 according to the seventh aspect of the present invention is schematically depicted.

The data processing system 40 may be a personal computer (PC), a laptop, a tablet, a server, a distributed system (e.g. cloud system) and the like. The data processing system 40 comprises a central processing unit (CPU) 41, a memory having a random access memory (RAM) 42 and a non-volatile memory (MEM, e.g. hard disk) 43, a human interface device (HID, e.g. keyboard, mouse, touchscreen etc.) 44 and an output device (MON, e.g. monitor, printer, speaker, etc.) 45. The CPU 41 RAM 42, HID 44 and MON 45 are communicatively connected via a data bus. The RAM 42 and MEM 43 are communicatively connected via another data bus. A trained NN that was trained with any of the methods according to the first, second and third aspect of the present invention and as schematically depicted in FIGS. 1 to 3 can be loaded into the RAM 32 from the MEM 33 or another computer-readable medium 20. Accordingly, the trained NN is implemented on the data processing system 40 and the CPU 41 can execute predictions based on provided input data and the trained weights of the trained NN. The execution can be initiated and controlled by a user via the HID 44. The status and/or result of the executed prediction by the trained NN may be indicated to the user by the MON 45. The result may be permanently stored on the non-volatile MEM 43 or another computer-readable medium.

In particular, the CPU 41 and RAM 42 for implementing the trained NN may comprise several CPUs 41 and several RAMs 42 for example in a computation cluster or a cloud system. The HID 44 and MON 45 for controlling execution of the prediction by the NN may be comprised by a different data processing system like a terminal communicatively connected to the data processing system 40 (e.g. cloud system).

Although specific embodiments have been illustrated and described herein, it will be appreciated by those of ordinary skill in the art that a variety of alternate and/or equivalent implementations exist. It should be appreciated that the exemplary embodiment or exemplary embodiments are only examples, and are not intended to limit the scope, applicability, or configuration in any way. Rather, the foregoing summary and detailed description will provide those skilled in the art with a convenient road map for implementing at least one exemplary embodiment, it being understood that various changes may be made in the function and arrangement of elements described in an exemplary embodiment without departing from the scope as set forth in the appended claims and their legal equivalents. Generally, this application is intended to cover any adaptations or variations of the specific embodiments discussed herein.

In the foregoing detailed description, various features are grouped together in one or more examples for the purpose of streamlining the disclosure. It is understood that the above description is intended to be illustrative, and not restrictive. It is intended to cover all alternatives, modifications and equivalents as may be included within the scope of the invention. Many other examples will be apparent to one skilled in the art upon reviewing the above specification.

Specific nomenclature used in the foregoing specification is used to provide a thorough understanding of the invention. However, it will be apparent to one skilled in the art in light of the specification provided herein that the specific details are not required in order to practice the invention. Thus, the foregoing descriptions of specific embodiments of the present invention are presented for purposes of illustration and description. They are not intended to be exhaustive or to limit the invention to the precise forms disclosed; obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. Throughout the specification, the terms "including" and "in which" are used as the plain-English equivalents of the respective terms "comprising" and "wherein," respectively. Moreover, the terms "first," "second," and "third," etc., are used merely as labels, and are not intended to impose numerical requirements on or to establish a certain ranking of importance of their objects. In the context of the present description and claims the conjunction "or" is to be understood as including ("and/or") and not exclusive ("either . . . or").

The invention claimed is:

1. A computer-implemented method of training a neural network, (NN), comprising the steps:
   receiving a training set T of training input data X=$(X_1, \ldots, X_n)$ and corresponding ground truth data Y=$(Y_1, \ldots, Y_n)$ for a predetermined number C of classes, where n>1 and C>=1; and
   training the NN, comprising the iterative training steps:
      selecting a training sub-set B of training input data $X_B$ and corresponding ground truth data $Y_B$ from the training set T, where 0<|B|<|T|;
      generating current outputs of the NN for the sub-set B by forward propagating the training input data $X_B$ of the training sub-set B in the NN;
      computing a categorical cross-entropy loss $L_{CCE}$ for the sub-set B based on the current outputs and the corresponding ground truth data $Y_B$ of the training sub-set B;
      computing a predictive entropy loss $L_S$ by removing non-misleading evidence from the current outputs and distributing the remaining current outputs over the predetermined number C of classes;
      computing a combined loss L by adding to the categorical cross-entropy loss $L_{CCE}$ the predictive entropy loss $L_S$ weighted with a predetermined first loss factor $\lambda_S$, where 0<=$\lambda_S$<=1;
      checking whether the training converged to a predefined lower limit for a convergence rate;
      updating weights of the NN based on the combined loss L and a predetermined training rate $\eta$, where 0<$\eta$<=1, in case the training did not converge; and
      stopping the training of the NN in case the training converged.

2. A computer-implemented method of training a neural network, NN, comprising the steps:
   receiving a training set T of training input data X=$(X_1, \ldots, X_n)$ and corresponding ground truth data Y=$(Y_1, \ldots, Y_n)$ for a predetermined number C of classes, where n>1 and C>=1; and
   training the NN, comprising the iterative training steps:
      selecting a training sub-set B of training input data $X_B$ and corresponding ground truth data $Y_B$ from the training set T, where 0<|B|<|T|;
      generating current outputs of the NN for the sub-set B by forward propagating the training input data $X_B$ of the training sub-set B in the NN;
      computing a categorical cross-entropy loss $L_{CCE}$ for the sub-set B based on the current outputs and the corresponding ground truth data $Y_B$ of the training sub-set B;
      sampling a perturbation level $\varepsilon_B$ randomly with a value from 0 to 1;
      generating an adversarial set $B_{adv}$ of adversarial input data $X_{adv}$ by applying a perturbation randomly selected from a predefined set of perturbations and weighted with the perturbation level $\varepsilon_B$ to the training input data $X_B$ of the training sub-set B, where $|X_{adv}|=|X_B|$;
      generating perturbed outputs of the NN for the adversarial set $B_{adv}$ by forward propagating the adversarial input data $X_{adv}$ of the adversarial set $B_{adv}$ in the NN;

computing an adversarial calibration loss $L_{adv}$ as the Euclidian norm, ($L_2$ norm) of an expected calibration error ECE, which takes a weighted average over the perturbed outputs grouped in a predefined number M of equally spaced bins each having an associated average confidence and accuracy, where M>1;

checking whether the training converged to a predefined lower limit for a convergence rate;

first time updating weights of the NN based on the categorical cross-entropy loss $L_{CCE}$ and a predetermined training rate η, where 0<η<=1, in case the training did not converge;

second time updating the weights of the NN based on the adversarial calibration loss $L_{adv}$ weighted with a predetermined second loss factor $\lambda_{adv}$, where 0<=$\lambda_{adv}$<=1, and the predetermined training rate η, in case the training did not converge; and stopping the training of the NN in case the training converged.

3. A computer-implemented method of training a neural network, (NN), comprising the steps:

receiving a training set T of training input data X=($X_1$, ..., $X_n$) and corresponding ground truth data Y=($Y_1$, ..., $Y_n$) for a predetermined number C of classes, where n>1 and C>=1; and training the NN, comprising the iterative training steps:

selecting a training sub-set B of training input data $X_B$ and corresponding ground truth data $Y_B$ from the training set T, where 0<|B|<|T|;

generating current outputs of the NN for the sub-set B by forward propagating the training input data $X_B$ of the training sub-set B in the NN;

computing a categorical cross-entropy loss $L_{CCE}$ for the sub-set B based on the current outputs and the corresponding ground truth data $Y_B$ of the training sub-set B;

computing a predictive entropy loss $L_S$ by removing non-misleading evidence from the current outputs and distributing the remaining current outputs over the predetermined number C of classes;

computing a combined loss L by adding to the categorical cross-entropy loss $L_{CCE}$ the predictive entropy loss $L_S$ weighted with a predetermined first loss factor $\lambda_S$, where 0<=$\lambda_S$<=1;

sampling a perturbation level $\varepsilon_B$ randomly with a value from 0 to 1;

generating an adversarial set $B_{adv}$ of adversarial input data $X_{adv}$ by applying a perturbation randomly selected from a predefined set of perturbations and weighted with the perturbation level $\varepsilon_B$ to the training input data $X_B$ of the training sub-set B, where $|X_{adv}|=|X_B|$;

generating perturbed outputs of the NN for the adversarial set $B_{adv}$ by forward propagating the adversarial input data $X_{adv}$ of the adversarial set $B_{adv}$ in the NN;

computing an adversarial calibration loss $L_{adv}$ as the Euclidian norm, ($L_2$ norm) of an expected calibration error ECE, which takes a weighted average over the perturbed outputs grouped in a predefined number M of equally spaced bins each having an associated average confidence and accuracy, where M>1;

checking whether the training converged to a predefined lower limit for a convergence rate;

first time updating weights of the NN based on the combined loss L and a predetermined training rate η, where 0<η<=1, in case the training did not converge;

second time updating the weights of the NN based on the adversarial calibration loss $L_{adv}$ weighted with a predetermined second loss factor $\lambda_{adv}$, where 0<=$\lambda_{adv}$<=1, and the predetermined training rate η, in case the training did not converge; and stopping the training of the NN in case the training converged.

4. The method according to claim 2, wherein the perturbation level $\varepsilon_B$ is randomly sampled from a perturbation level set ε including a predefined number of values from 0 to 1, preferably from 0 to 0.5, and most preferably including the values 0, 0.05, 0.1, 0.15, 0.2, 0.25, 0.3, 0.35, 0.4, 0.45.

5. The method according to claim 2, wherein the predefined set of perturbations includes image-based perturbation types or word-based perturbation types.

6. The method according to claim 1, further comprising the subsequent step:

evaluating a robustness of the trained NN by:

providing the trained NN with a first set of multiple perturbed input datasets, which have been perturbed with a perturbation of a first perturbation-type, wherein each input dataset has been perturbed with a different predefined perturbation level $\varepsilon_B$;

generating perturbed outputs of the NN based on the provided first set of multiple perturbed input datasets;

computing expected calibration errors (ECEs) for the respective generated perturbed outputs for the first set of multiple perturbed input datasets;

providing the trained NN with at least one further set of multiple perturbed input datasets, which have been perturbed with a perturbation of at least one further perturbation-type, wherein each input dataset has been perturbed with a different predefined perturbation level $\varepsilon_B$;

generating perturbed outputs of the NN based on the provided at least one further set of multiple perturbed input datasets;

computing the ECEs for the respective generated perturbed outputs for the further of multiple perturbed input datasets set; and calculating micro-averaged ECEs across the generated outputs of each provided set of multiple perturbed input datasets by calculating the average of the respective ECEs.

7. A computer executing a computer program comprising instructions which cause the computer to carry out the steps of the method according to claim 1.

8. A non-transitory computer-readable medium having stored thereon the computer program according to claim 7.

9. A data processing system for carrying out the steps of the method according to claim 1.

10. A data processing system comprising a NN trained with the steps of the method according to claim 1.

* * * * *